United States Patent
Andes et al.

(10) Patent No.: US 6,500,251 B1
(45) Date of Patent: *Dec. 31, 2002

(54) MULTI-COATED INTERFERENCE PIGMENTS

(75) Inventors: Stephanie Andes, Maintal (DE); Gerd Bauer, Kleinostheim (DE); Günter Brenner, Griesheim (DE); Dieter Brückner, Darmstadt (DE); Michael Schmelz, Kriftel (DE); Andrea Heyland, Ober-Kainsbach (DE); Matthias Kuntz, Seeheim (DE); Karl Osterried, Dieburg (DE); Gerhard Pfaff, Münster (DE)

(73) Assignee: Merck Patent Gesellschaft mit beschrankter Haftung, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,260

(22) PCT Filed: May 23, 1997

(86) PCT No.: PCT/EP97/02652

§ 371 (c)(1), (2), (4) Date: Mar. 9, 1999

(87) PCT Pub. No.: WO98/53012

PCT Pub. Date: Nov. 26, 1998

(51) Int. Cl.$^7$ ................................................. C04B 1/32

(52) U.S. Cl. ....................... 106/415; 106/436; 106/437; 106/438; 106/439; 106/446; 106/441; 106/442

(58) Field of Search ................................. 106/436, 437, 106/438, 439, 446, 441, 442, 415

(56) References Cited

U.S. PATENT DOCUMENTS

| | | | | |
|---|---|---|---|---|
| 3,395,203 A | | 7/1968 | Morita ........................ | 106/436 |
| 3,767,443 A | | 10/1973 | Clark et al. .................. | 106/436 |
| 4,168,986 A | | 9/1979 | Venis .......................... | 106/436 |
| 4,882,133 A | * | 11/1989 | Saegusa ...................... | 423/335 |
| 5,958,125 A | * | 9/1999 | Schmid et al. .............. | 106/417 |
| 6,238,472 B1 | * | 5/2001 | Andes et al. ................ | 106/430 |
| 6,280,520 B1 | * | 8/2001 | Andes et al. ................ | 106/415 |

* cited by examiner

Primary Examiner—Elizabeth D. Wood
(74) Attorney, Agent, or Firm—Millen, White, Zelano & Branigan

(57) ABSTRACT

Multilayer interference pigment consisting of plateletlike titanium dioxide as carrier material, coated with alternating layers of metal oxides of low and high refractive index, the difference in the refractive indices being at least 0.1, which is obtainable by solidification and hydrolysis of an aqueous solution of a thermally hydrolyzable titanium compound on a continuous belt, detachment of the resulting coat, coating of the resulting titanium dioxide platelets, with or without drying in between, by a wet method with, alternately, a metal oxide hydrate of high refractive index and a metal oxide hydrate of low refractive index by hydrolysis of the corresponding, water-soluble metal compounds, separation, drying and, if desired, calcining of the material obtained.

12 Claims, 1 Drawing Sheet

MULTI-COATED INTERFERENCE PIGMENTS

The invention relates to multilayer interference pigments with plateletlike titanium dioxide as substrate.

Multilayer pigments of low transparency are known. The metal oxide layers are prepared either in a wet process, by precipitating the metal oxide hydrates from a metal salt solution onto a carrier material, or by vapour deposition or sputtering under reduced pressure. In general, the vapour deposition processes are too complex and costly for mass production of pigments. Thus U.S. Pat. No. 4,434,010 describes a multilayer interference pigment consisting of a central layer of a reflecting material (aluminium) and alternating layers of two transparent, dielectric materials of high and low refractive index, for example titanium dioxide and silicon dioxide, either side of the central aluminium layer. This pigment is employed for the printing of securities.

JP H7-759 (Kokoku) describes a multilayer interference pigment with a metallic lustre. It consists of a substrate coated with alternating layers of titanium dioxide and silicon dioxide. The substrate is formed from flakes of aluminium, gold or silver or from platelets of mica and glass which are coated with metals. Accordingly, it is a typical metal-effect pigment. This pigment is of high opacity. For applications where a high level of transparency of the pigmented material is required, for example for agricultural films, the pigment is unsuitable. Furthermore, it has the disadvantage that the depth effect typical of interference pigments is not produced since, owing to the total reflection of the light at the metal layer which forms the core, a number of pigment particles are unable to enter into interaction. The interference effect therefore remains limited to the coats located on the metal layer.

Mica is the substrate employed most frequently for the production of interference pigments.

Mica pigments are used widely in the printing and coating industries, in cosmetics and in polymer processing. They are distinguished by interference colours and a high lustre. For the formation of extremely thin coats, however, mica pigments are not suitable, since the mica itself, as a substrate for the metal oxide coats of the pigment, has a thickness of from 200 to 1200 nm. A further disadvantage is that the thickness of the mica platelets in some cases varies markedly about a mean value. Moreover, mica is a naturally occurring mineral which is contaminated by foreign ions. Furthermore, technically highly complex and time-consuming processing steps are required including, in particular, grinding and classifying.

Pearl lustre pigments based on thick mica platelets and coated with metal oxides have, owing to the thickness of the edge, a marked scatter fraction, especially in the case of relatively fine particle-size distributions below 20 $\mu$m.

As a substitute for mica it has been proposed to use thin glass flakes which are obtained by rolling of a glass melt with subsequent grinding. Indeed, interference pigments based on such materials exhibit colour effects superior to those of conventional, mica-based pigments. Disadvantageous, however, is that the glass flakes have a very large mean thickness of about 10–15 $\mu$m and a very broad thickness distribution (typically between 4 and 20 $\mu$m), whereas the thickness of interference pigments is typically not more than 3 $\mu$m.

EP 0,384,596 describes a process in which hydrated alkali metal silicate is subjected at temperatures of 480–500° C. to the action of an air jet, forming bubbles with thin walls; the bubbles are subsequently comminuted to give platelet-like alkali metal silicate substrates with a thickness of less than 3 $\mu$m. However, the process is complex and the thickness distribution of the resulting platelets is relatively broad.

DE 11 36 042 describes a continuous belt method of preparing plateletlike or glitterlike oxides or oxide hydrates of metals of groups IV and V and of the iron group of the Periodic Table. In this method, a release layer comprising, for example, a silicone coating is first of all applied, if desired, to a continuous belt in order to facilitate the subsequent detachment of the metal oxide layer. Then a liquid film is applied which comprises a solution of a hydrolysable compound of the metal which is to be converted into the desired oxide, and the film is dried and subsequently detached using a vibration device. The coat thickness of the platelets obtained is given as being from 0.2 to 2 $\mu$m, although no concrete examples of this are cited.

EP 0 240 952 and EP 0 236 952 propose a continuous belt method of preparing different plateletlike materials, including silicon dioxide, aluminium oxide and titanium dioxide. In this method, a thin liquid film of defined thickness of a precursor of the plateletlike material is applied, via a roller system, to a smooth belt; the film is dried and detached from the belt, forming plateletlike particles. The particles are subsequently, if desired, calcined, ground and classified.

The thickness of the platelets obtained in accordance with the method described in EP 0 240 952 is relatively well defined, since the film is applied very uniformly, for example to the continuous belt via a roller system. The layer thickness of the platelets is given in the examples as being from 0.3 to 3.0 $\mu$m. According to Example 1, a first roller is wetted with the precursor used by immersing this roller partially into a stock container which is filled with the precursor. The film is transferred from this roller to a second, co-rotating roller which is in very close contact with the first roller. Finally, the film is rolled off from the second roller onto the continuous belt.

Disadvantages, however, are the use of very expensive precursor materials and, in particular, the increased requirements in terms of workplace safety which must be applied when organometallic compounds are used. The complete chemical conversion of the precursor into the desired coating material requires, in general, high heating of the film and of the belt material. In addition to the considerable thermal stress which this places on the belt material, the high energy consumption and the restriction on the process speed are also highly disadvantageous for the economy of the method.

WO 93/08 237 describes plateletlike pigments consisting of a plateletlike matrix comprising silicon dioxide, which may contain soluble or insoluble colourants and which is coated with one or more reflecting layers of metal oxides or metals. The plateletlike matrix is prepared by solidification and hydrolysis of water glass in a continuous belt.

DE 12 73 098 describes the preparation of a mother-of-pearl pigment by vapour deposition of ZnS, $MgF_2$, ZnO, $CaF_2$ and $TiO_2$ films on to a continuous belt. This process however, like the process described in U.S. Pat. No. 4,879,140 in which plateletlike pigments with Si and $SiO_2$ coats are obtained by plasma deposition from $SiH_4$ and $SiCl_4$, is associated with very high expenditure on apparatus.

The object of the invention is to provide an essentially transparent interference pigment having strong interference colours and/or a strong angular dependency of the interference colours. Furthermore, the object of the invention is to provide a pigment which consists only of optically functional layers and is therefore extremely thin.

This object is achieved in accordance with the invention by a multilayer interference pigment consisting of plateletlike titanium dioxide as carrier material, coated with alternating layers of metal oxides of low and high refractive index, the difference in the refractive indices being at least 0.1, which is obtainable by solidification and hydrolysis of an aqueous solution of a thermally hydrolysable titanium compound on a continuous belt, detachment of the resulting coat, coating of the resulting titanium dioxide platelets, with or without drying in between, by a wet method with, alternately, a metal oxide hydrate of high refractive index and a metal oxide hydrate of low refractive index by hydrolysis of the corresponding, water-soluble metal compounds, separation, drying and, if desired, calcining of the material obtained.

This object is additionally achieved in accordance with the invention by a process for preparing the novel pigment, in which an aqueous solution of a thermally hydrolysable titanium compound is applied as a thin film to a continuous belt, the liquid film is solidified by drying, during the course of which the titanium dioxide is developed from the solution by means of a chemical reaction, the resulting layer is subsequently detached from the belt and washed, the titanium dioxide platelets obtained, with or without drying in between, are suspended in water and coated with, alternately, a metal oxide hydrate of high refractive index and a metal oxide hydrate of low refractive index, by addition and hydrolysis of the corresponding, water-soluble metal compounds, and the coated titanium dioxide platelets are separated out from the aqueous suspension, dried and, if desired, calcined.

The invention additionally relates to the use of the novel pigments for pigmenting paints, printing inks, plastics, cosmetics and glazes for ceramics and glass and for producing agricultural films.

For this purpose they can be employed as mixtures with commercially available pigments, for example inorganic and organic absorption pigments, metal-effect pigments and LCP pigments.

The novel pigments are based on plateletlike titanium dioxide. These platelets have a thickness of between 10 nm and 500 nm, preferably between 40 and 150 nm. The extent in the two other dimensions is between 2 and 200 $\mu$m and, in particular, between 5 and 50 $\mu$m.

The metal oxide of high refractive index can be an oxide or mixture of oxides with or without absorbent properties, for example $TiO_2$, $ZrO_2$, $Fe_2O_3$, $Fe_3O_4$, $Cr_2O_3$ or ZnO, or a compound of high refractive index such as, for example, iron titanates, iron oxide hydrates and titanium suboxides, or mixtures and/or mixed phases of these compounds with one another or with other metal oxides.

The metal oxide of low refractive index is $SiO_2$, $Al_2O_3$, ALOOH, $B_2O_3$ or a mixture thereof and can likewise have absorbent or nonabsorbent properties. If desired, the oxide layer of low refractive index may contain alkali metal oxides and alkaline earth metal oxides as constituents.

The thickness of the layers of the metal oxides of high and low refractive index is critical for the optical properties of the pigment. Since a product with strong interference colours is desired, the thicknesses of the layers must be adjusted relative to one another. If n is the refractive index of a layer and d its thickness, the colour which appears in a thin layer is the product of n and d, i.e. the optical thickness. The colours of such a film, as produced with normal incidence of light in reflected light, result from an intensification of the light of wavelength $\lambda=(4/2N-1).nd$ and by attenuation of light of wavelength $\lambda=(2/N.nd)$, where N is a positive integer. The variation in colour which takes place as the thickness of the film increases results from the intensification or, respectively, attenuation of particular wavelengths of the light by interference. For example, a 115 nm thick film of titanium dioxide of refractive index 1.94 has an optical thickness of 115×1.94=223 nm, and light of wavelength 2×223 nm=446 nm (blue) is attenuated in the course of reflection, with the result that the reflected light is yellow. In the case of multilayer pigments, the interference colour is determined by the intensification of specific wavelengths and, if two or more layers in a multilayer pigment possess the same optical thickness, the colour of the reflected light becomes more intense and full as the number of layers increases. Moreover, by a suitable choice of the layer thicknesses it is possible to achieve a particularly marked variation of colour in dependency on the viewing angle. A pronounced colour flop develops, which may be desirable for the pigments according to the invention. The thickness of the individual metal oxide layers, independently of their refractive index, is therefore from 20 to 500 nm, preferably from 50 to 300 nm.

The number and thickness of the layers is dependent on the desired effect. Normally, the desired effects are achieved if the 5-layer system $TiO_2/SiO_2/TiO_2/SiO_2/TiO_2$ is built up and if the thicknesses of the individual layers are matched optically to one another. When using optically relatively thin $TiO_2$ layers (layer thickness <100 nm) it is possible, for example, to produce interference pigments with a blue colour which, with a substantially smaller $TiO_2$ content, are stronger in colour and more transparent than pure $TiO_2$-mica pigments. The saving in terms of $TiO_2$ is up to 80% by weight. By means of the precipitation of thick $SiO_2$ layers (layer thickness >100 nm), pigments having a strongly pronounced angular dependency of the interference colour are obtained.

By precipitating further $SiO_2$ and $TiO_2$ layers it is also possible to obtain higher systems, the number of layers then being limited by the economics of the pigment.

Since, in contrast to mica, plateletlike titanium dioxide as substrate is an optically functional layer, covering the substrate with, for example, two layers of the abovementioned structure gives an interference system comprising 5 thin layers of sharply defined thicknesses. The reflection or transmission spectrum of such a pigment exhibits finer and more precisely matchable structures than the spectrum of a corresponding pigment based on a substrate with a broad thickness distribution, such as mica.

Even with extremely thin $TiO_2$ layers (layer thickness: 40 nm), these pigments exhibit strong interference colours. The angular dependency of the interference colour is also particularly pronounced. This extreme colour flop is not observed with conventional metal oxide-mica pigments.

The novel pigments are prepared in a two-stage process. In the first stage, plateletlike titanium dioxide particles are prepared with the aid of a continuous belt.

Figure 1:
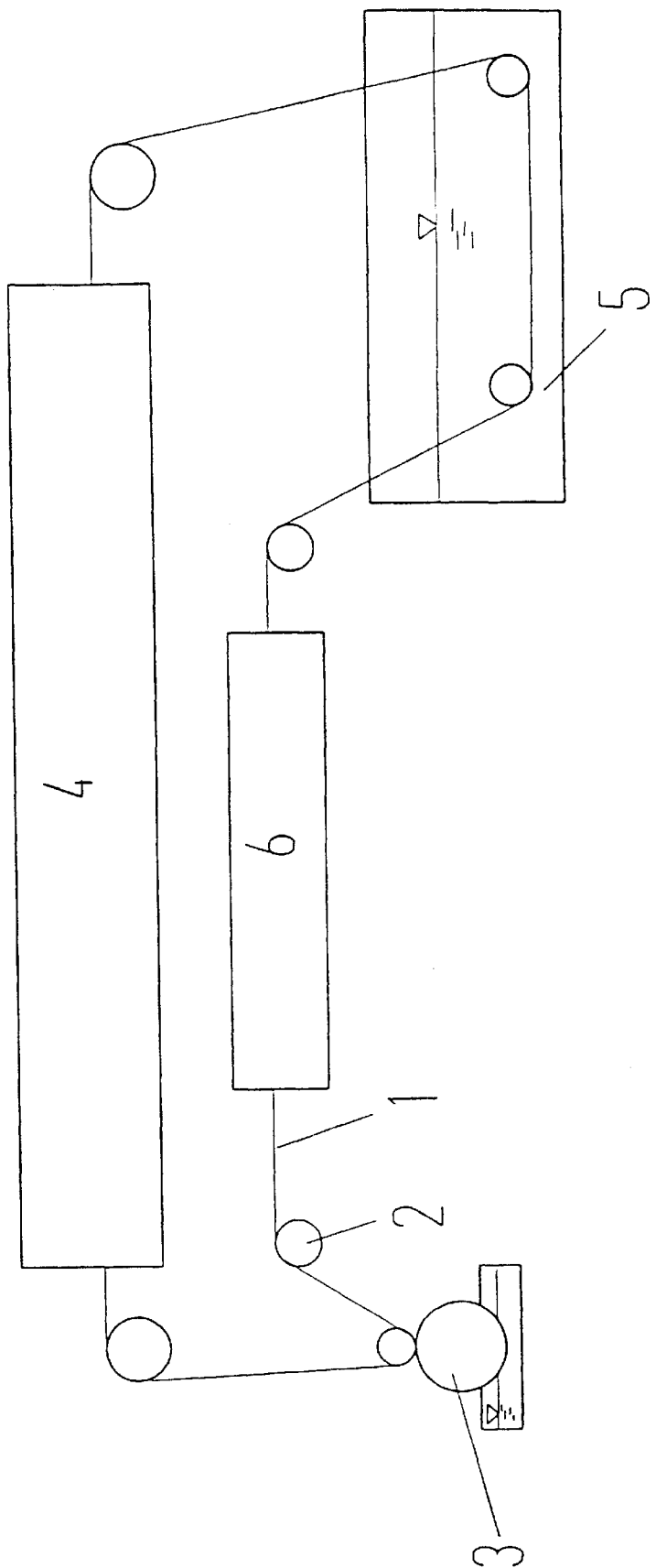
FIG. 1: Belt Method

First of all, the belt method will be explained with reference to FIG. 1.

The continuous belt 1, which is guided via a roller system 2, passes through an applicator unit 3 in which it is coated with a thin film of an aqueous solution of a thermally hydrolysable titanium compound. Preference is given to the use of an aqueous titanium tetrachloride solution. The concentration of the titanium salt in these solutions is from 7 to 30% by weight, preferably from 8 to 15% by weight. Suitable applicator units which can be employed are roller applicators and also flow-type units. The belt speed is between 2 and 400 m/min, preferably 5–200 m/min.

In order to achieve uniform wetting of the plastics belt it is expedient to add a commercially available wetting agent to the coating solution or to activate the surface of the belt by flame treatment, corona treatment or ionization.

The coated belt passes subsequently through a drying section 4 in which the coat is dried at temperatures between 30 and 200° C. As dryers it is possible, for example, to employ commercially available infrared, circulating-air jet and UV dryers.

After passing through the drying section the belt is passed through the detachment baths 5 containing an appropriate detachment medium, for example deionized water, where the dried layer is removed from the belt. The detachment procedure is supported by additional devices, for example jets, brushes or ultrasound.

In a subsequent dryer 6, the belt is dried before being coated again.

The continuous belt should be made from a chemically and thermally resistant plastic in order to ensure an adequate service life and high drying temperatures. Suitable materials for the belt include polyethylene terephthalate (PET) or other polyesters and polyacrylates.

The film width is typically between a number of centimetres and two or more metres. The thickness is between 10 $\mu$m and a number of millimetres, these two parameters being optimized in respect of the particular requirements.

Further details of continuous belt methods are known from U.S. Pat. No. 3,138,475, EP 0 240 952 and WO 93/08 237.

In a second stage, the titanium dioxide platelets detached from the belt are coated, without being dried beforehand, with, in alternation, a metal oxide hydrate of low refractive index and a metal oxide hydrate of high refractive index.

The metal oxide layers are preferably applied by a wet-chemical process which may be one of the wet-chemical coating techniques developed for the preparation of pearl lustre pigments; techniques of this kind are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or else in further patent documents and other publications.

In the case of wet coating, the substrate particles are suspended in water, and one or more hydrolysable metal salts are added at a pH which is suitable for the hydrolysis and is chosen so that the metal oxides and/or metal oxide hydrates are precipitated directly onto the platelets without any instances of secondary precipitation. The pH is usually kept constant by simultaneous metered addition of a base. The pigments are then separated off, washed and dried and, if desired, calcined, it being possible to optimize the calcining temperature with respect to the particular coating present. If desired, the pigments to which individual coatings have been applied can be separated off, dried and, if desired, calcined before being resuspended in order to apply the further layers by precipitation.

Furthermore, coating can also be carried out in a fluidized-bed reactor by gas-phase coating, in which context it is possible, for example, to employ correspondingly the techniques proposed for the preparation of peal lustre pigments in EP 0 045 851 and EP 0 106 235.

The metal oxide of high refractive index used is preferably titanium dioxide, and the metal oxide of low refractive index preferably used is silicon dioxide.

For the application of the titanium dioxide layers the process described in U.S. Pat. No. 3,553,001 is preferred.

An aqueous titanium salt solution is added slowly to a suspension, heated to about 50–100° C., in particular 70–80° C., of the material to be coated, and a substantially constant pH of about 0.5–5, in particular about 1.5–2.5, is maintained by simultaneous metered addition of a base, for example aqueous ammonia solution or aqueous alkali metal hydroxide solution. As soon as the desired layer thickness of the $TiO_2$ precipitation has been reached, the addition of the titanium salt solution and of the base is stopped.

This method, which is also called the titration method, is notable for the fact that it avoids an excess of titanium salt. This is achieved by supplying to the hydrolysis only that quantity per unit time which is necessary for uniform coating with the hydrated $TiO_2$ and which can be adsorbed per unit time by the available surface area of the particles to be coated. There is therefore no production of hydrated titanium dioxide particles not precipitated on the surface to be coated.

For the application of the silicon dioxide layers, the following process is to be employed: a sodium silicate solution is metered into a suspension, heated to about 50–100° C., in particular 70–80° C., of the material to be coated. The pH is held constant at 7.5 by simultaneous addition of 10% hydrochloric acid. As soon as the desired layer thickness of the $SiO_2$ precipitation has been reached, the addition of the silicate solution is stopped. Stirring is carried out subsequently for 30 minutes.

The wet-chemical production of two or more interference layers of high and low refractive index with precisely defined thicknesses and a smooth surface on finely divided plateletlike substrates has not been disclosed to date. It should be noted that it is necessary first of all to apply a metal oxide of low refractive index to the transparent carrier material.

It is additionally possible to subject the finished pigment to an aftercoating or aftertreatment process which further increases the stability to light, weather and chemicals, or which facilitates the handling of the pigment, especially its incorporation into different media. Suitable aftercoating and aftertreatment processes are those described, for example, in DE-C 22 15 191, DE-A 31 51 354, DE-A 32 35 017 or DE-A 33 34 598.

The substances applied additionally make up only from about 0.1 to 5% by weight, preferably from about 0.5 to 3% by weight, of the overall pigment.

In addition, the novel pigment can also be coated with firmly adhering inorganic or organic colourants of low solubility. Preference is given to the use of colour lakes and, in particular, of aluminium colour lakes. For this purpose a layer of aluminium hydroxide is applied by precipitation and in a second step is laked with a colour lake. The process is described in more detail in DE 24 29 762 and DE 29 28 287.

Preference is also given to an additional coating with complex salt pigments, especially cyanoferrate complexes, for example Prussian blue and Turnbull's blue, as is described in EP 0 141 173 and DE 23 13 332.

The novel pigment can also be coated with organic dyes and, in particular, with phthalocyanine or metal phthalocyanine and/or indanthrene dyes in accordance with DE 40 09 567. To this end a suspension of the pigment in a solution of the dye is prepared and this solution is then combined with a solvent in which the dye is of low or zero solubility.

Furthermore, metal chalcogenides or metal chalcogenide hydrates and carbon black can also be employed for an additional coating.

The examples which follow are intended to illustrate the invention in more detail without limiting it.

EXAMPLE 1

A circulating belt of polyethylene terephthalate (width: 0.3 m, speed: 20 m/min) is coated with a 20% titanium tetrachloride solution by means of a counterrotating applicator roll. The coating solution contains 0.3% by weight of surfactant (DISPERSE-AYD W-28, manufacturer: DANIEL PRODUCTS COMPANY). The aqueous film on the belt is dried in a drying section by subjecting it to hot air at 70° C., and the layer formed is detached from the belt in a detachment basin filled with deionized water. The titanium dioxide platelets are filtered and washed with deionized water. The platelets have a silvery lustre and a coat thickness of 100±10 nm.

For further coating, they are either redispersed in deionized water or dried at 110° C.

EXAMPLE 2
5-layer System of $TiO_2/SiO_2/TiO_2/SiO_2/TiO_2$
1) $SiO_2$ Layer 50 g of $TiO_2$ flakes having a yellow interference colour (particle size <20 μm) are suspended in 1.5 l of deionized water and the suspension is heated to 75° C. 270 ml of a sodium silicate solution (125 g of $SiO_2$/l) are metered into this suspension at 75° C. over the course of 90 minutes. During this addition the pH is held constant at 7.5 with 10% hydrochloric acid. When addition is over, stirring is carried out at 75° C. for 30 minutes in order to complete the precipitation.

2) $TiO_2$ Layer

The pH of the suspension is lowered to 2.2 with 10% hydrochloric acid, and 590 ml of an aqueous $TiCl_4$ solution (400 g of $TiCl_4$/l) are metered in over the course of 3 h. Throughout the addition the pH is held constant at 2.2 with 32% NaOH solution. When addition is over, stirring is carried out at 75° C. for a further 30 minutes in order to complete the precipitation.

The mixture is then allowed to cool to room temperature and the pigment obtained is filtered off, washed salt-free with deionized water and dried at 110° C. The pigment is then calcined at 700° C. for 30 minutes. The pigment thus obtained exhibits a brilliant, golden interference colour which is substantially more intense than that of the starting material.

EXAMPLE 3
5-layer System of $TiO_2/SiO_2/TiO_2/SiO_2/TiO_2$ with a Blue Interference Colour
1) $SiO_2$ Layer 40 g of $TiO_2$ flakes having a silver interference colour are suspended in 1.5 l of deionized water and the suspension is heated to 75° C. 580 ml of a sodium silicate solution (125 g of $SiO_2$/l) are metered into this suspension at 75° C. over the course of 180 minutes. During this addition the pH is held constant at 7.5 with 10% hydrochloric acid. When addition is over, stirring is carried out at 75° C. for 30 minutes in order to complete the precipitation.

2) $TiO_2$ Layer

The pH of the suspension is lowered to 2.2 with 10% hydrochloric acid, and 470 ml of an aqueous $TiCl_4$ solution (400 g of $TiCl_4$/l) are metered in over the course of 120 min. Throughout the addition the pH is held constant at 2.2 with 32% NaOH solution. When addition is over, stirring is carried out at 75° C. for a further 30 minutes in order to complete the precipitation.

The mixture is then allowed to cool to room temperature and the pigment obtained is filtered off, washed salt-free with deionized water and dried at 110° C. The pigment is then calcined at 700° C. for 30 minutes.

The pigment thus obtained exhibits a deep-blue interference colour.

What is claimed is:

1. A multilayer interference pigment comprising:
    platelet shaped titanium dioxide as carrier material, coated with alternating layers of metal oxides of low refractive index and colorless non-absorbing metal oxides of high refractive index, each layer having a thickness of from 20 to 500 nm, the difference in the refractive indices being at least 0.1, which is obtained by solidification and hydrolysis of an aqueous solution of a thermally hydrolysable inorganic titanium compound on a continuous belt, detachment of the resulting coat, whereby a platelet shaped titanium dioxide pigment is formed, coating of the resulting titanium dioxide platelets, with or without drying in between, by a wet method with, alternately, a metal oxide hydrate of low refractive index and a colorless non-absorbing metal oxide hydrate of high refractive index by hydrolysis of the corresponding, water soluble inorganic metal compounds, separation, drying and, optionally, calcining of the material obtained.

2. An interference pigment according to claim 1, wherein said colorless non-absorbing metal oxide of high refractive index is $TiO_2$, $ZrO_2$, $ZnO$ or a mixture of these oxides.

3. An interference pigment according to claim 1, wherein the metal oxide of low refractive index is $SiO_2$, $Al_2O_3$, $AlOOH$, $B_2O_3$ or a mixture thereof, and optionally alkali metal oxides and alkaline earth metal oxides being present as additional constituents.

4. A composition for a paint, printing ink, plastic, cosmetic, agricultural film or glaze for ceramics and glass, containing an interference pigment according to claim 1.

5. A pigment according to claim 4, wherein the pigment is employed as a mixture with commercially available pigments.

6. A multilayer interference pigment according to claim 1, wherein said platelet shaped titanium dioxide has a thickness of between 10 nm and 500 nm.

7. A multilayer interference pigment according to claim 6, wherein said platelet shaped titanium dioxide has a thickness of between 40 nm and 150 nm.

8. A multilayer interference pigment according to claim 6, wherein said platelet shaped titanium dioxide has an extent in the other two other dimensions of between 5 μm and 50 μm.

9. A multilayer interference pigment according to claim 7, wherein said platelet shaped titanium dioxide has an extent in the other two other dimensions of between 5 μm and 50 μm.

10. A multilayer interference pigment according to claim 1, wherein the thickness of the individual layers of said metal oxides of high refractive index and metal oxides of low refractive index is between 20 to 500 nm.

11. A multilayer interference pigment according to claim 10, wherein the thickness of the individual layers of said metal oxides of high refractive index and metal oxides of low refractive index is between 50 to 300 nm.

12. A multilayer interference pigment comprising:

platelet shaped titanium dioxide as carrier material, coated with alternating layers of metal oxides of low refractive index and colorless non-absorbing metal oxides of high refractive index, the difference in the refractive indices being at least 0.1, which is obtained by solidification and hydrolysis of an aqueous solution of a thermally hydrolysable inorganic titanium compound on a continuous belt, detachment of the resulting coat, whereby a platelet shaped titanium dioxide pigment is formed, coating of the resulting titanium dioxide platelets, with or without drying in between, by a wet meat with, alternately, a metal oxide hydrate of low refractive index and a colorless non-absorbing metal oxide hydrate of high refractive index by hydrolysis of the corresponding, water soluble inorganic metal compounds, separation, drying and, optionally, calcining of the material obtained, with the proviso that the pigment does not have any additional layer containing carbon black, metal chalcogenide, metal chalcongenide hydrate, inorganic or organic colorant, complex salt pigment or organic dye.

* * * * *

UNITED STATES PATENT AND TRADEMARK OFFICE
CERTIFICATE OF CORRECTION

PATENT NO. : 6,500,251 B1  Page 1 of 1
DATED : December 31, 2002
INVENTOR(S) : Stephanie Andes et al.

It is certified that error appears in the above-identified patent and that said Letters Patent is hereby corrected as shown below:

Column 10,
Line 2, reads "wet meat," should read -- wet method, --.

Signed and Sealed this

Twenty-seventh Day of January, 2004

JON W. DUDAS
*Acting Director of the United States Patent and Trademark Office*